United States Patent [19]

Kaihatsu

[11] Patent Number: 4,961,493
[45] Date of Patent: Oct. 9, 1990

[54] AROMATIC PACKAGE

[75] Inventor: Noboru Kaihatsu, Ohsaka, Japan

[73] Assignee: Nisshinbo Industries, Inc., Nihonbashi, Japan

[21] Appl. No.: 449,761

[22] Filed: Dec. 13, 1989

[30] Foreign Application Priority Data

Dec. 27, 1988 [JP] Japan .......................... 63-167635[U]

[51] Int. Cl.⁵ ........................ F17G 13/00; B65D 85/00
[52] U.S. Cl. .................... 206/0.5; 206/524.1; 206/524.2
[58] Field of Search ................... 206/0.5, 524.1, 524.2, 206/524.3, 484.1, 439

[56] References Cited

U.S. PATENT DOCUMENTS

| | | | | |
|---|---|---|---|---|
| 1,960,149 | 5/1934 | Gilot | .................................... | 206/0.5 |
| 1,983,691 | 12/1934 | Bonardi | .............................. | 206/0.5 |
| 3,239,145 | 3/1966 | Russo | .................................... | 206/0.5 |

FOREIGN PATENT DOCUMENTS

| | | | |
|---|---|---|---|
| 2063860 | 6/1972 | Fed. Rep. of Germany | ....... 206/0.5 |
| 1307903 | 9/1962 | France | ................. 206/0.5 |
| 2329539 | 5/1977 | France | ................. 206/0.5 |

*Primary Examiner*—William I. Price
*Attorney, Agent, or Firm*—Rogers & Killeen

[57] ABSTRACT

An aromatic package comprises a liquid or gel type aromatic and a sack made of a gas-permeable but liquid-impermeable film and hermetically receiving the aromatic. In another form of the aromatic package of the invention, the above-mentioned aromatic package is received in a gas-permeable case which in turn is hermetically sealed in a gas-impermeable packaging member. In use, the packaging member is broken and the case is placed in, for example, a house room or compartment of a motor vehicle, so that the fragrance or aroma is released and floats on the air.

6 Claims, 2 Drawing Sheets

AROMATIC PACKAGE

BACKGROUND OF THE INVENTION

1. Field of the Invention

The present invention relates to an aromatic package which makes a fragrance or an aroma float on the air in a room of a house, compartment of a motor vehicle. The aromatic package of the invention can be brought in handbag or a suitcase, so that when the bag or the suitcase is opened, an aroma is freed to the air. The aromatic package also may be put in a pocket of a suit or in a tamoto of a kimono so that an aroma is suspended in the air around the wearer.

2. Description of the Prior Art

In general, aromatics are used in liquid, wax or granular forms. Aromatics in the form of a wax or granules, however, are disadvantageous in that the aromatic in the core portion can hardly be dissipated, so the aroma is progressively weakened after dissipation of the aromatic from the surface region. Therefore, in order to enjoy the fragrance or aroma stably for a long time, aromatics are preferably used in the form of liquids or gels.

Liquid or gel type aromatics, however, suffer from the following disadvantages.

(1) A liquid or gel type aromatic, when charged in a bottle or the like capped with a cap having holes or pores, will flow out of the bottle if the bottle has fallen down.

(2) The same problem is encountered when the liquid aromatic or gel type is charged in a bottle or the like packaging member capped with a material which produces a capillary action such as a non-woven cloth or a sponge.

(3) In general, a liquid or gel type aromatic is usually dissolved in a solvent which is a mixture of ethanol and water. In such a case, the ethanol evaporates quicker than water so that only the aroma component dissolved in ethanol dissipates, resulting in a change in the aromatic composition of the liquid in the packaging member and a consequent change in the nature of aroma.

SUMMARY OF THE INVENTION

Accordingly, an object of the present invention is to provide an aromatic package which makes use of a liquid or gel aromatic and which can overcome the above-described problems of the prior art.

To this end, according to the present invention, there is provided an aromatic package comprising: a liquid or gel type aromatic and a sack made of a gas-permeable but liquid-impermeable film. The invention also provides an aromatic package of the type mentioned above, further comprising a gas-permeable case receiving the sack; and a gas-impermeable packaging member in which the case is hermetically sealed.

The liquid or gel type aromatic used in the present invention can be prepared by dissolving a liquid or powder aromatic in a solvent such as water, ethanol or a mixture of water and ethanol, or by gelling the liquid or powder aromatic by means of a suitable gelling agent. Examples of the gelling agents are polymers such as polyvinyl alcohol and polyacrylates, polysaccharides such as mannan, sodium alginate and so forth, and polysaccharide derivatives such as carboxy methyl cellulose, methylcellulose and so forth.

Various types of films can be used as the gas-permeable liquid-impermeable film such as a thermoplastic polyurethane, ethylene-vinylacetate copolymer and so forth. The most suitable film, however, is a thermo-plastic polyurethane film formed by a melting method (inflation method, calendering method, extrusion forming and so forth). This type of film generally exhibits an adequate gas-permeability and is most preferred from the viewpoints of softness, strength and anti-cold characteristics. The thickness of the gas-permeable liquid-impermeable film preferably ranges about 30 to 500$\mu$.

This film provides a uniform permeability to gases even when a water-ethanol mixture is used as the solvent. For forming a liquid aromatic containing sack, an ordinary method can be used, which comprises, for example, charging a sack with the liquid aromatic and heat-sealing the sack. A similar method can be used when a gel aromatic is used.

The aromatic package having an aromatic contained in a gas-permeable but liquid impermeable sack used as an aromatic package as it is or, alternatively, the sack is then placed in a case which is made of a plastic or metal having pores or a sheet material having excellent gas-permeability, and the case is hermetically packaged in a packaging material of a sealing plastic film packaging member, whereby the aromatic package of the invention is obtained. The film may be a polyester film, polyethylene film, polyvinylidene chloride film, or the like.

The aromatic package of the present invention, having an aromatic sealed in a gas-permeable but liquid impermeable sack can be sold or stocked as it is. The purchaser or user places the sack somewhere in a house room or an automotive compartment, so that the aroma is released into the room or compartment. When the sack is carried by being, for example, placed in a pocket, the aroma is made to float on the air so as to extinguish any offensive smell or to enjoy persons therearound with good fragrance or aroma. When the aromatic package mentioned above is placed in a gas-permeable case which in turn is packaged by a packaging material such as gas-impermeable film, the user opens the package to extract the case and places the case somewhere in a house room or an automotive compartment, so that the aroma is released into the room or compartment. When the case is carried by being, for example, placed in a pocket, the aroma is made to float on the air so as to extinguish any offensive smell or to enjoy persons therearound with good fragrance or aroma. This type of aromatic package is advantageous in that the case protects the sack against any damaging external force which may be caused when the package is collided by an obstacle.

The aromatic is sealed in the sack, so the liquid or gel content does never flow out regardless of the angle at which it is held, and any risk for the environment to be contaminated with the liquid or gel can be avoided.

In addition, effective period of use of the aromatic package can be freely designed by suitably selecting the factors such as the thicknesses of the films, size of the package and the quantity of the aromatic charged in the package.

The above and other objects, features and advantages of the present invention will become clear from the following description of the preferred embodiments when the same is read in conjunction with the accompanying drawings.

DESCRIPTION OF THE PREFERRED EMBODIMENT

Figure 1:
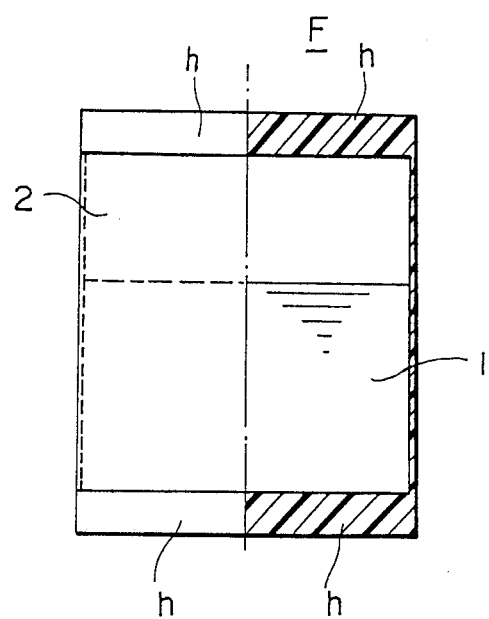
FIGS. 1 and 2 are front elevational views of embodiments of the aromatic package of the present invention, with their right half parts shown in sections.
Figure 2:
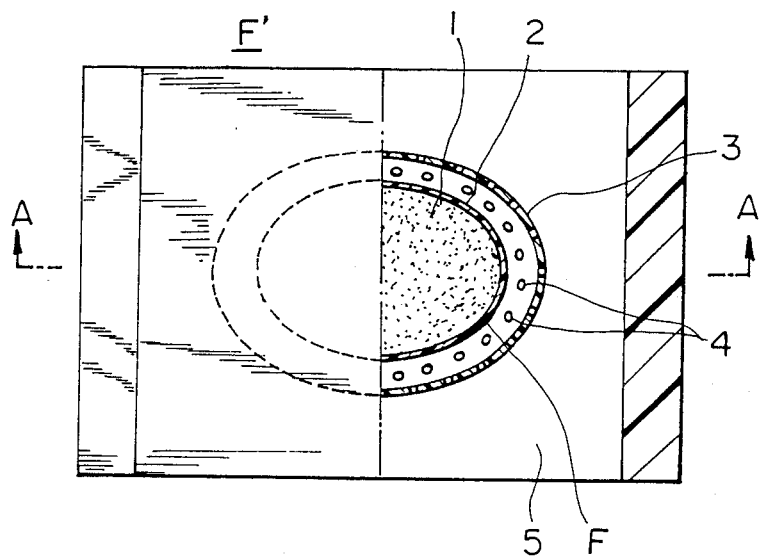
Figure 3:
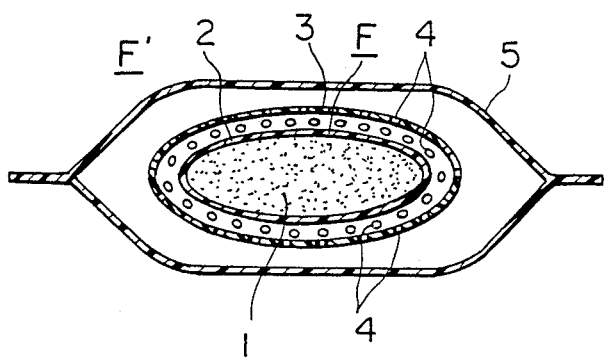
FIG. 3 is a sectional view which is taken along the line A—A of FIG. 2.

A preferred embodiment of the present invention will be described with reference to the accompanying drawings. Referring to FIGS. 1 and 2, a liquid or gel aromatic 1 is charged in a sack 2 of the aforementioned gas-permeable liquid-impermeable polyurethane film which allows gases to pass therethrough while blocking any liquid. The sack 2 and the aromatic 1 charged therein form a first form of aromatic package F of the present invention.

The sack 2 of polyurethane film is encased in a plastic or metal case 3 which has a multiplicity of pores 4. The case 3 is hermetically sealed in a packaging member 5 made of a plastic film which is gas-impermeable. The aromatic package F, the case 3 accommodating the aromatic package F and the packaging material 5 in combination form a second form of the aromatic package F' of the present invention.

In an example, a polyurethane film of 150μ thick was used as the film 2, while using, as the liquid aromatic 1, an aromatic (produced by ST Kagaku, Chalane-α, floral fragrance), dissolved in a solvent containing 50 wt % of ethanol and 50 wt % of water. The liquid aromatic 1 was charged in an amount of 2.5 ml in the sack made of the above-mentioned film, whereby an aromatic package F having a permeation area of 12 cm² was obtained. The thus obtained aromatic package F was suspended in the air in a room of a temperature of about 25° C. and the strength of the aroma and rate of reduction of weight of the aromatic were measured. The weight reduction was about 40 %, while the strength of aroma was never reduced, after elapse of 40 days.

On the other hand, the aromatic gel 1 was prepared by dissolving an aromatic (Chalene, —α floral fragrance, produced by ST Kagaku) in a solvent composed of 50 wt % of ethanol and 50 wt % of water so as to form a solution and adding carboxy methanol cellulose as a gelling agent into the solution so as to gel the solution. The aromatic gel 1 thus prepared was charged in amount of 2.5 ml in the sack 2 of polyurethane film, whereby another aromatic package F of the present invention, having a permeation area of 12 cm² was obtained.

The above-mentioned aromatic package F was placed in the case 3. The case 3 was then hermetically sealed in the sealed plastic film packaging member 5, whereby an aromatic package F' of the invention was obtained. The aromatic package thus obtained was opened and the case 3 picked out of the sealed plastic film packaging member 5, was hung in the air within a room maintained at about 25° C. as in the cases of the aromatic packages F for the purpose of measurement of the level or strength of the aroma and the change in the weight of the aromatic gel 1. The results were substantially the same as those confirmed with the aromatc packages F.

The aromatic package of the present invention is quite convenient for use in house rooms, automotive compartments, as well as for carrying, and can be used without substantial difficulty at a reasonable cost.

What is claimed is:

1. An aromatic package for creating an aroma comprising:
    an aromatic substance for creating an aroma as said substance evaporates, said aromatic substance comprising a liquid solvent, and an aromatic agent dissolved in said solvent so that a solution of said solvent and said agent is formed;
    a sealed sack for containing said aromatic substance, said sack comprising a gas-permeable and liquid-impermeable polyurethane film 30 to 500 microns thick adapted to hold said substance and sealed to prevent the loss of said substance in nongaseous form from said sack when said sack is held in any position, while allowing the aroma created by said substance to permeate through said film; and
    a case for holding said sack containing said aromatic substance, said case having a multiplicity of pores so that the aroma permeating through said film is released from said case.

2. The aromatic package as defined in claim 1 further comprising a gas-impermeable seal enclosing said case so that the aroma released by said case does not reach the air surrounding the seal.

3. The aromatic package as defined in claim 1 wherein said aromatic substance further comprises a gelling agent to gel said solution.

4. The aromatic package as defined in claim 1 wherein said sack does not comprise an absorbent material for absorbing said aromatic substance.

5. The aromatic package as defined in claim 1 wherein said substance contains approximately one milliliter of said aromatic agent for each five square centimeters of surface area of said sack.

6. The aromatic package as defined in claim 1 wherein said liquid solvent comprises nearly equal parts water and ethanol.

* * * * *